United States Patent [19]
Takeuchi et al.

[11] Patent Number: 5,800,343
[45] Date of Patent: Sep. 1, 1998

[54] ENDOSCOPE LIGHT GUIDE CONNECTOR ALLOWING ADJUSTMENT OF THE ANGLE OF INCIDENT LIGHT RAYS

[75] Inventors: Shinji Takeuchi; Haruo Akiba, both of Omiya, Japan

[73] Assignee: Fuji Photo Optical Co., Ltd., Omiya, Japan

[21] Appl. No.: 792,388

[22] Filed: Feb. 3, 1997

Related U.S. Application Data

[63] Continuation of Ser. No. 515,005, Aug. 14, 1995, abandoned.

[30] Foreign Application Priority Data

Aug. 18, 1994 [JP] Japan .................. 6-215247

[51] Int. Cl.⁶ ........................................ A61B 1/07
[52] U.S. Cl. ............................... 600/132; 600/178
[58] Field of Search ........................ 600/178, 180, 600/182, 167, 132, 160

[56] References Cited

U.S. PATENT DOCUMENTS

| | | | |
|---|---|---|---|
| 3,090,379 | 5/1963 | Ferris et al. | 600/179 |
| 4,416,268 | 11/1983 | Hagino | 600/132 |
| 4,483,585 | 11/1984 | Takami | 600/182 X |
| 4,589,404 | 5/1986 | Barath et al. | 600/182 X |
| 4,704,007 | 11/1987 | Landre et al. | 600/167 X |
| 4,929,070 | 5/1990 | Yokota et al. | 600/182 X |
| 5,036,834 | 8/1991 | Sugiyama et al. | 600/182 |

*Primary Examiner*—John P. Leubecker
*Attorney, Agent, or Firm*—Oblon, Spivak, McClelland, Maier & Neustadt, P.C.

[57] ABSTRACT

An endoscopic light guide connector of the type which has an input end of a light guide fitted in a light guide rod to be inserted into a connector socket at a connection port of a light source to locate a light pickup end face of the light guide at a light condensing position of a condenser lens of the light source. The light guide connector includes an adaptor pipe which is detachably fitted on a fore end portion of the light guide rod and which is fitted with a corrective lens to adjust angles of incident light rays from the condenser lens of the light source on the basis of a numerical aperture of the light guide for receiving input light rays at a maximum acceptance angle or at angles close to a maximum acceptance angle of the light guide. An adjustor unit fixedly receives the light guide rod and adjusts the distance between the input end of the light guide and the condenser lens.

5 Claims, 5 Drawing Sheets

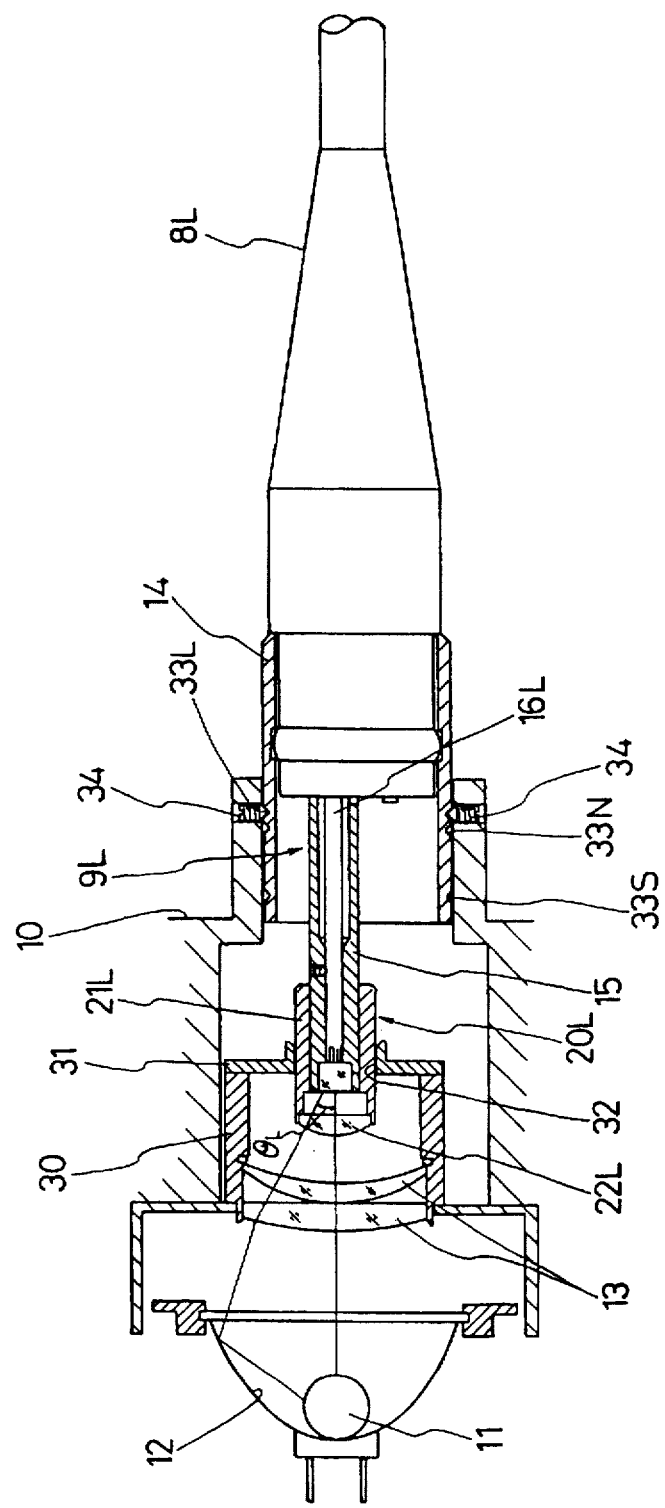

ENDOSCOPE LIGHT GUIDE CONNECTOR ALLOWING ADJUSTMENT OF THE ANGLE OF INCIDENT LIGHT RAYS

This application is a Continuation of application Ser. No. 08/515,005, filed on Aug. 14, 1995, now abandoned.

BACKGROUND OF THE INVENTION

1. Field of the Art

This invention relates to a light guide connector for endoscopes in medical use, and more particularly to a light guide connector capable of connecting endoscopic light guides of different optical characteristics to one illumination light source in an optimum condition in terms of light transmission efficiency.

2. Prior Art

Endoscopes which are generally resorted to in medical examinations of intracavitary portions or other dark internal regions invariably need a supply of illumination light to a spot under observation. For this purpose, an endoscope is usually connected to an illumination light source which is arranged to condense light rays from a source lamp toward a predetermined position by the use of a concave reflector lamp and a condenser lens. On the other hand, a light guide is extended through the entire length of the endoscope in order to transmit illumination light rays to an observation spot efficiently without substantial losses in transmission. More particularly, the light guide is extended, on one side of a manipulating head assembly of the endoscope, through an insertion rod portion of the endoscope with a light emitting end face at its fore output end located in an illumination window at the distal end of the insertion rod, and, on the other side of the manipulating head assembly, through a flexible complex cable with a light pickup end face at its proximal input end fitted in a light guide rod of a light guide connector which is detachably connectable to a mating connector socket on the part of the light source. The light guide connector is arranged such that, when the light guide rod is plugged into the connector socket on the light source, the light pickup end face of the light guide is located at the position toward which input light rays are condensed by the light source.

The input light rays incident on the light pickup end face at the proximal end of the light guide, which is fitted in the light guide rod, are transmitted through the entire length of the light guide to its light emitting end which is disposed in the illumination window at the distal end of the insertion rod of the endoscope to illuminate an intracavitary region under observation. In this regard, for transmitting the input light efficiently from the light source to the light emitting end of the light guide without losses, the input light rays from the source lamp should fall on the light pickup end face of the light guide at angles smaller than a maximum light acceptance angle of the light guide. More specifically, in transmitting light rays, a light guide usually utilizes a difference in refractivity between its core and clad materials in such a way that input light rays make a travel forward by repeating reflections on boundary surfaces between the core and clad materials. In this regard, in order to suppress light losses to a minimum, total reflections should take place on the boundary surfaces. The maximum acceptance angle corresponds to the maximum angle of incidence for the total reflections between the core and clad materials, and is expressed by a product of a sine of the acceptance angle with the light pickup face of the light guide and a difference in refractivity between the core and clad materials, the maximum acceptance angle being generally referred to as "numerical aperture (N.A.)." Namely, $N.A.=n_0 \cdot \sin \theta = (n_1^2 - n_2^2)^{1/2}$ (where $n_0$=the refraction index of the medium, $\theta$=the angle of incidence with the light pickup end face, $n_1$=the refraction index of the core, and $n_2$=the refraction index of the clad). Accordingly, the light guide has an intrinsic numerical aperture depending upon the properties of its component materials. On the other hand, the light source, which is arranged to condense illumination light beams toward a predetermined position, has a specific light condensing angle as determined by the characteristics of its source lamp, reflector mirror and condenser lens.

Now, considering behaviors of illumination light rays at the light emitting (output) end of the light guide, it is desirable to diffuse the illumination light over a broad range for securing a broad illuminated view field in observation. To this end, a diffuser lens is normally fitted in the illumination window at the distal end of the insertion rod of the endoscope. However, in order to project the illumination light uniformly over a broader range, it is desirable for the illumination light rays to undergo diffusion as much as possible upon being projected from the output end of the light guide. In this regard, the angle of light projection from the output end of the light guide corresponds to the aforementioned light acceptance angle, so that the light guide is preferred to have as large a light acceptance angle as possible.

In short, for the purpose of efficient loss-free transmission of illumination light through the light guide and projection of illumination light over a broader range, light guides are generally arranged to receive input light rays at a maximum acceptance angle or at angles close to the maximum acceptance angle, optimizing the maximum angle of incidence of input light rays from the light source on the basis of a given numerical aperture. Therefore, an endoscopic light source is usually designed to permit connection of a light guide of a specific type, namely, a light guide of a specific numerical aperture because connection of light guides of other numerical apertures would give rise to a number of problems such as increased light losses in transmission, a restricted or narrow illumination range, irregularities in illumination light level across an irradiated intracavitary region etc. For these reasons, it has been considered difficult to use one light source universally for a variety of endoscopes with light guides of different numerical apertures.

SUMMARY OF THE INVENTION

In view of the situations as explained above, it is a primary object of the present invention to provide a light guide connector which makes it possible to use one light source commonly for a number of endoscopic light guides of different optical characteristics particularly in numerical aperture.

In accordance with the present invention, the above-stated objective is achieved by the provision of an endoscopic light guide connector of the type having an input end of a light guide fitted in a light guide rod to be inserted into a connector socket at a connection port of a light source to locate a light pickup end face of the light guide at a light condensing position of the light source, characterized in that the light guide connector comprises an adaptor pipe fitted on a fore end portion of the light guide rod and having a corrective lens element in a path of input light rays from a light condensing means of the light source to the light pickup end face of the light guide to optimize angles of incident light rays from the light condensing means on the basis of a numerical aperture of the light guide.

When connecting an endoscope to a light source which is optically arranged in agreement with the numerical aperture of a light guide on the endoscope, the light guide connector can be simply plugged into the light source without using an adaptor. However, in case a connecting light guide is of a numerical aperture which is incongruous with a light source, the angle of incident light rays from the light source is adjusted into an optimum angle by the use of an adaptor at a stage anterior of a light pickup end face at a proximal input end of the light guide. More particularly, in case a light guide has a smaller numerical aperture, an adaptor with a concave lens is fitted on the light guide connector to adjust the condensing angle of input light rays into agreement with the smaller numerical aperture which determines the maximum light acceptance angle of the light guide. By doing so, illumination light rays from the light source can be transmitted efficiently through the light guide with the least possible losses. On the other hand, in case of a light guide which has a larger numerical aperture, transmission losses of input illuminating light rays at the light pickup end of the light guide would be of only a minimum amount, if any, despite the disagreement in numerical aperture. Therefore, in such a case it is not of utmost necessity to use an adaptor with a corrective lens on the connector. However, in order to broaden the angle of light projection from the output end of the light guide, it is preferable to use an adaptor with a convex lens which brings the angle of incidence of input light rays as close to the maximum acceptance angle of the light guide as possible.

Preferably, the adaptor is detachably threaded on a fore end portion of the light guide rod. On the part of the light source, the connector socket which receives the light guide connector is preferably provided with an aligning aperture in a holder member which is located on the front side of a condenser lens housing in such a way that the adaptor and the light guide are retained in an optically aligned position relative to the condenser lens of the light source upon plugging the light guide connector into the connector socket.

The above and other objects, features and advantages of the invention will become apparent from the following description of the invention, taken in conjunction with the accompanying drawings which show by way of example preferred embodiments of the invention.

BRIEF DESCRIPTION OF THE DRAWINGS

In the accompanying drawings:

FIG. 5 is a view similar to FIGS. 3 and 4, but showing an endoscopic light guide connector with an adaptor for another different light guide.

DESCRIPTION OF PREFERRED EMBODIMENTS

Figure 1:
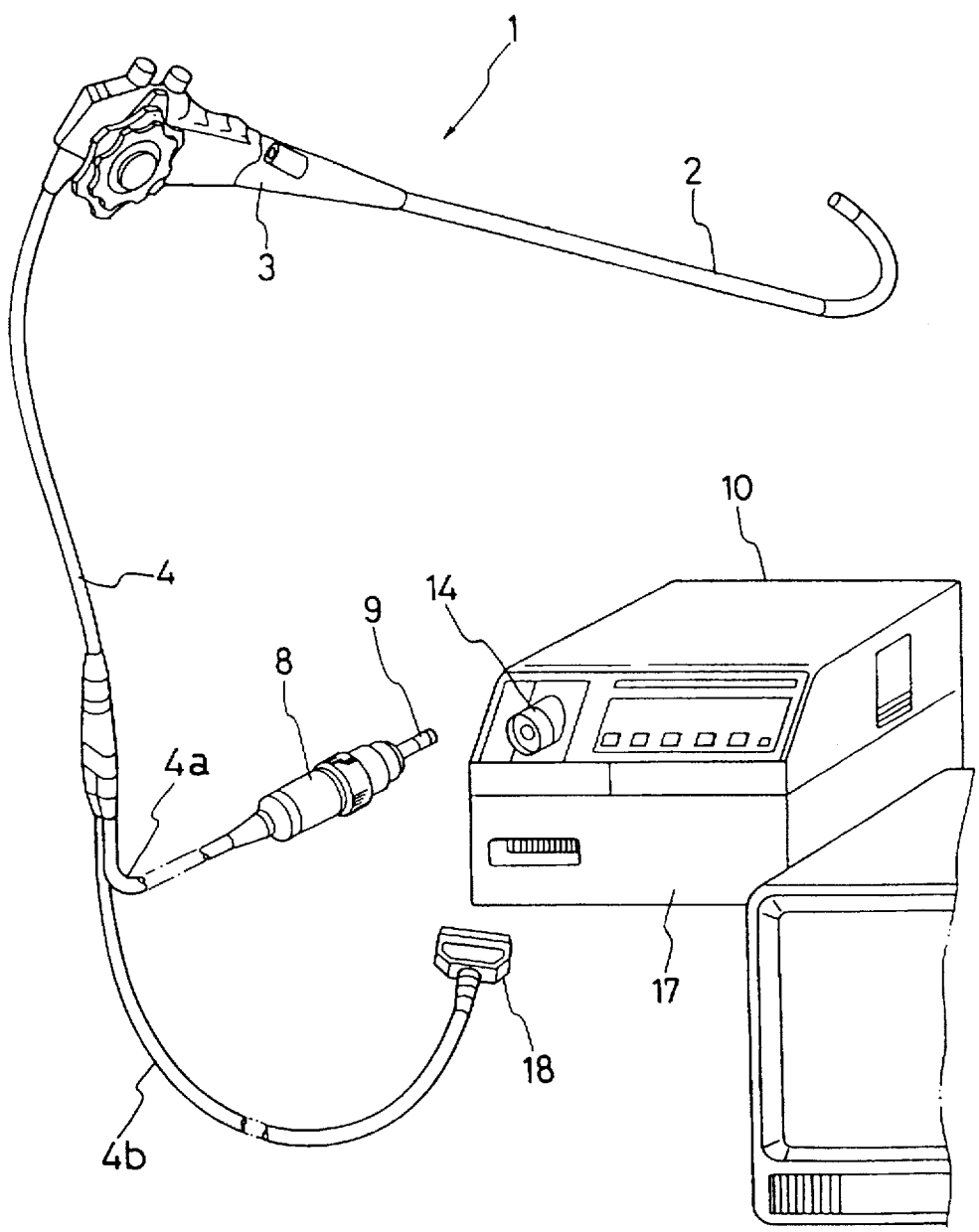
FIG. 1 is a schematic general view of an endoscopic examination system including an endoscope and an endoscopic light source.

Hereafter, the invention is described more particularly by way of its preferred embodiments shown in the drawings.

Figure 2:
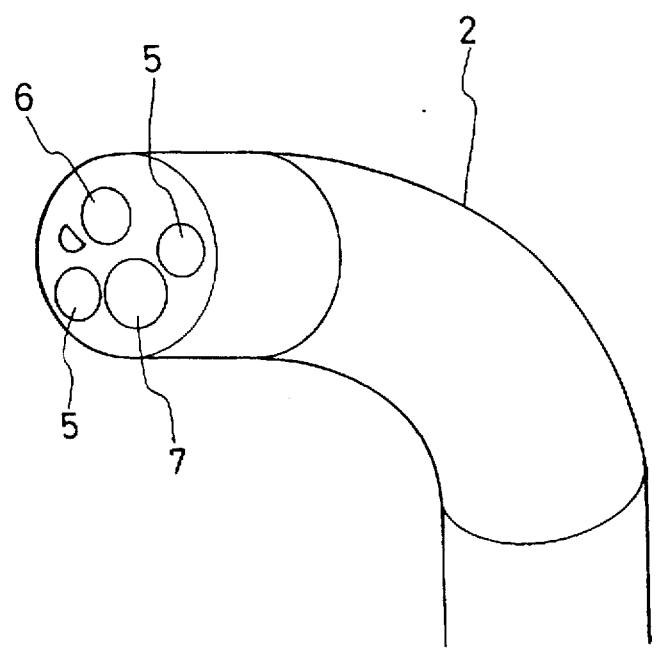
FIG. 2 is a schematic outer view of a fore end portion of an endoscopic insertion rod.

Referring first to FIG. 1, there are shown major components of an endoscopic examination system, including an endoscope 1 having a flexible insertion rod 2, a manipulating head assembly 3 connected to the proximal end of the insertion rod 2, and a flexible connection cable 4 extended from the manipulating head assembly 3 and containing a light guide cable 4a and an electrical signal cable 4b. As shown in FIG. 2, illumination windows 5 and an observation window 6 are opened on a distal end face of the insertion rod 2 along with an exit opening of a biopsy channel 7 which is provided coextensively in the insertion rod 2 for introduction of forceps or other instruments.

Figure 3:
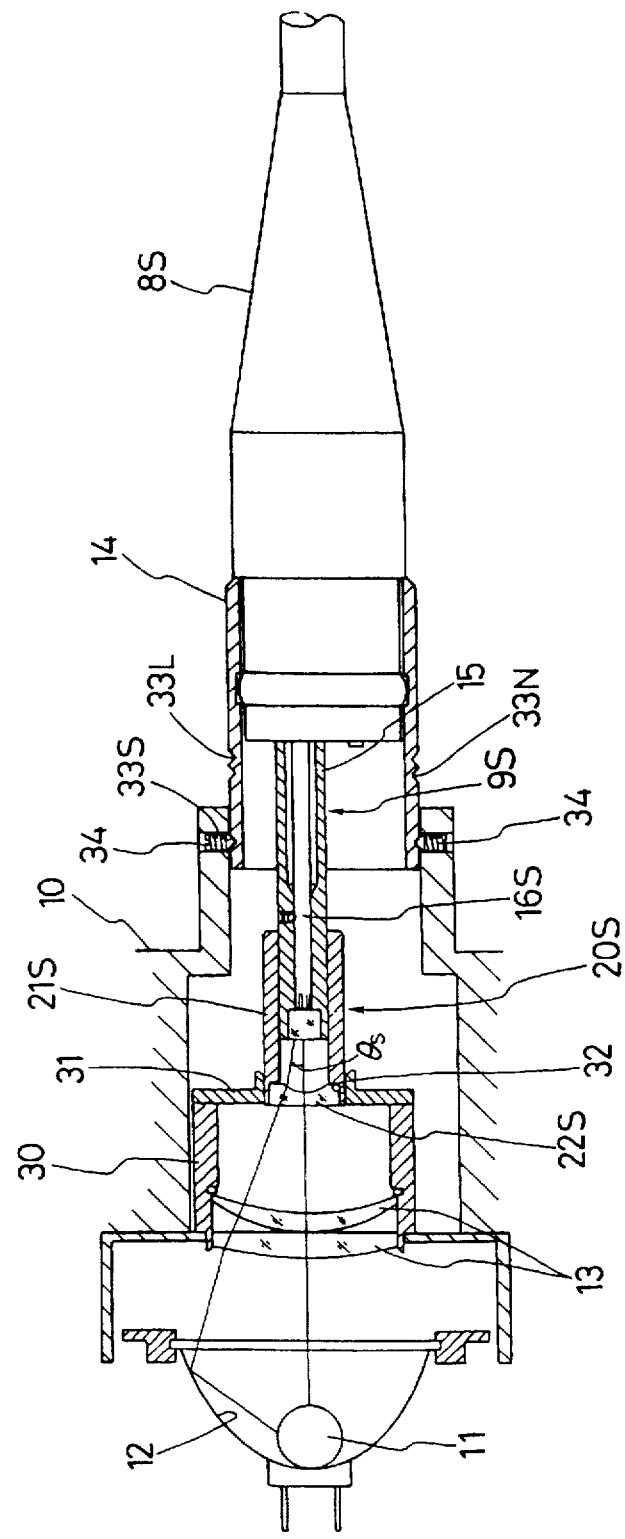
FIG. 3 is a partly sectioned view of an endoscopic light guide connector plugged into a socket on a light source enclosure.
Figure 4:
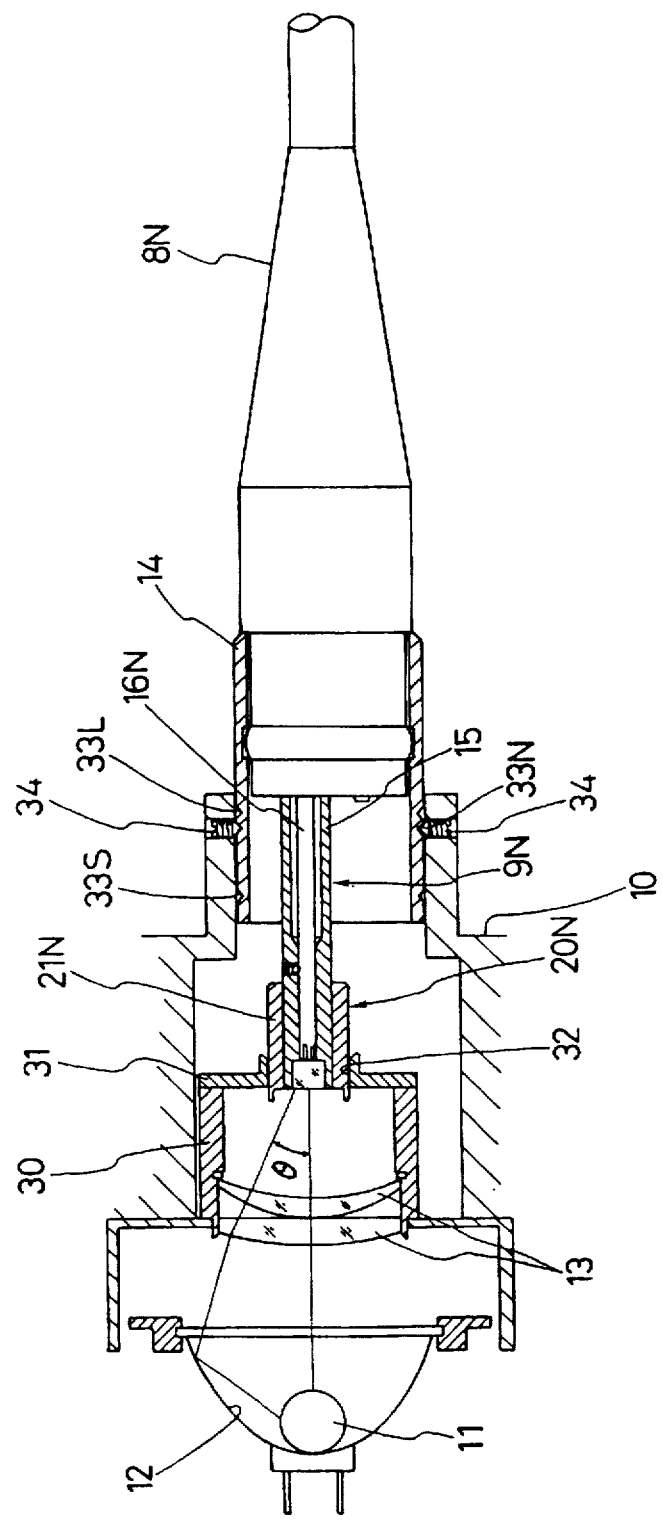
FIG. 4 is a view similar to FIG. 3 but showing an endoscopic light guide connector with an adaptor for a different light guide, which is different in numerical aperture from the light guide of FIG. 3.

The flexible light guide cable 4b is terminated with a light guide connector 8 with an axially projecting light guide rod 9. For connection to a light source 10, this light guide connector 8 is extractably plugged into a connector socket 14 at a connection port of the light source 10 which is internally provided with a source lamp 11, a concave reflector mirror 12 and a condenser lens 13 as shown in FIGS. 3 to 5. The connector socket 14 which is fitted in the connection port of the light source 10 is dimensioned and positioned such that the fore end of the light guide rod 9 is located at a light condensing position of the condenser lens 13 when the light guide connector 8 is plugged into the socket 14.

The light guide rod 9 is constituted by a cylindrical metal sheath 15 which securely wraps in a proximal input end portion of a light guide 16. The just-mentioned light guide 16 is constituted by a bundle of a multitude of ultra-fine fiber optics, and extended from the light guide rod 9 through the connection cable 4 and the manipulating head assembly 3 down to the illumination windows 5 at the distal end of the insertion rod 2 of the endoscope 1. The connection cable 4 is bifurcated in its proximal end portion into the light guide cable 4a and the electrical signal cable 4b with a connector 18 for connection to a signal processor 17.

The light guide rod 9 has an adaptor removably fitted on its fore end portion to correct the angle of incidence of input illumination light rays to the light guide 16. As mentioned hereinbefore, the light guide 16 has an intrinsic numerical aperture as determined by its core and clad materials, and its maximum angle of light acceptance is determined by the value of its numerical aperture. On the other hand, the light source 10 has a particular light condensing angle which is determined by the characteristics of the source lamp 11, reflector mirror 12 and condenser lens 13. Therefore, the adaptor serves to correct the condensing angle of input light rays from the condenser lens 13 into conformity with a numerical aperture of a light guide which is plugged into the light source 10, thereby to ensure a maximum pickup volume of input illumination light and minimum light losses in transmission to the light guide, along with a wider projection angle of illumination light toward an intracavitary region under observation.

In this regard, FIG. 3 shows a light guide connector 8S which is plugged into the socket 14 of the light source 10, the light guide connector 8S having in its light guide rod 9S a light guide 16S of a smaller numerical aperture, that is, a smaller maximum light acceptance angle as compared with the light condensing angle of the condenser lens 13 of the light source 10. On the other hand, FIG. 4 shows a light guide connector 8N which is plugged into the socket 14 of the same light source 10, the light guide connector 8N having in its light guide rod 9N a light guide 16N of a numerical aperture in agreement with the light condensing angle of the light source 10. Further, in relation with the same light source 10, FIG. 5 shows a light guide connector 8L which has in its light guide rod 9L a light guide 16L of a larger numerical aperture for the light source 10.

As seen in FIGS. 3 to 5, three different types of adaptor pipes 20S, 20N and 20L are threaded on fore end portions of light guide rods 9S, 9N and 9L, respectively. These adaptor pipes 20S, 20N and 20L are formed in the same size in outer diameter. Of these three adaptor pipes 20S, 20N and 20L, no corrective lens is fitted in the cylindrical body 21N of the adaptor pipe 20N on the light guide rod 9N, which encases the light guide 16N of a numerical aperture appropriate for the light condensing angle of the light source 10. On the other hand, corrective lenses 22S and 22L are fitted in the adaptor pipes 21S and 21L on the light guide rods 9S and 9L with light guides 16S and 16L of smaller and larger numerical apertures, respectively. The corrective lenses 22S and 22L are removable.

More specifically, the corrective lens 22S which is fitted in the adaptor pipe 20S for the light guide with a smaller numerical aperture is a concave lens. Accordingly, past the condenser lens 13 of the light source 10, the illumination light rays which would be incident on the light guide 16S at a condensing angle of θ are corrected through the adaptor lens 22S into a condensing angle of $θ_n$ which is smaller than θ. Consequently, the light acceptance angle of the light guide 16S is adjusted by the adaptor lens 22S into agreement with its numerical aperture to maximize its light pickup volume and at the same time to minimize the light losses in transmission.

In contrast, the corrective lens 22L which is fitted in the adaptor 20L for the light guide 16L of a larger numerical aperture is a convex lens. Therefore, the illumination light rays which are condensed at the angle of θ through the condenser lens 13 of the light source 10 are adjusted through the adaptor lens 22L into an angle $θ_L$ which is larger than the angle θ. In this instance, the light guide 16L has a larger numerical aperture, so that a greater acceptance angle, corresponding to the increased condensing angle $θ_L$, contributes to widen the projection angle at the output end of the light guide without entailing greater light losses in transmission. As a consequence, the adaptor makes it possible to illuminate intracavitary regions uniformly over a broader range.

As mentioned above, the adaptor pipes 20S, 20N and 20L threaded on the light guide rods 9S, 9N and 9L are all of the same size in outer diameter, so that they fit in an aligning aperture 32 which is formed in a holder plate 31 on the front side of a housing 30 of the condenser lens 13. The aperture 32 is formed in a slightly larger diameter than the outside diameter of the adapters 20S, 20N and 20L and, when the light guide connector 8 is plugged into the socket 14 on the light source 10, serves to receive and hold a fore end portion of the light guide rod 9S, 9N or 9L in a predetermined optically aligned position, namely, serves to hold the optical axis of the light guide 16S, 16N or 16L substantially in alignment with that of output illumination light rays from the condenser lens 13 of the light source 10.

Thus, depending upon the numerical aperture of the light guide, a corrective lens or no lens is fitted on the adaptor, using a concave lens 22S for a light guide of a small numerical aperture as in the case of the adaptor 20S and a convex lens 22L for a light guide of a large numerical aperture as in the case of the adaptor 20L. On the other hand, since the source lamp 11, reflector mirror 12 and condenser lens 13 on the part of the light source 10 are all mounted fixedly, the distance between the condenser lens 13 and the light pickup end of the light guide needs to be varied from one light guide to another depending upon which one of the light guide rods 9S, 9N and 9L is connected to the light source 10.

In order to locate the light pickup ends of the light guides 16S, 16N and 16L at a correct position relative to the condenser lens 13, the socket member 14, serving as an adjustor unit, on the light source enclosure wall is adjustable into appropriate positions prior to receiving the light guide connectors 8S, 8N and 8L which have the adaptor pipes 20S, 20N and 20L fitted on the light guide rods 9S, 9N and 9L, respectively. Namely, set screws 34 are threaded radially inward through the connection port 10a on the light source enclosure 10 to engage in one of three V-shaped grooves 33S, 33N and 33L which are formed around the circumference of the socket member 14 for fixing same in one of three different positions. More specifically, when connecting to the light source 10 the light guide rod 9S which has the adaptor pipe 20S, the socket member 14 is fixed in position for the light guide rod 9S by threading the set screws 34 into engagement with the circumferential groove 33S. When connecting the light guide rod 9N which is fitted with the adaptor pipe 20N, the socket member 14 is fixed in position on the connection port 10a by threading the set screws 34 into engagement with the circumferential groove 33N. Further, when connecting the light guide rod 9L which is fitted with the adaptor pipe 20L, the socket member 14 is fixed in position on the connection port 10a by threading the set screws 34 into engagement with the circumferential groove 33L.

Thus, the light guide connector with the above-described arrangements according to the invention makes it possible to connect to one and single light source a number of endoscopes with light guides of different numerical apertures. For instance, let us assume here that the light source 10 has the source lamp 11, reflector mirror 12 and condenser 13 arranged to supply illumination light rays at a condensing angle which suits for the light guide 16N with a numerical aperture (N.A.)=0.66.

In case of an endoscope with a light guide of the same numerical aperture as the light guide 16N, the lensless adaptor pipe 20N is threaded on the light guide rod 9N. At the same time, the socket member 14 on the light source 10 is fixed in position by anchoring the set screws 34 in the V-groove 33N on the socket member 14. In this state, as shown in FIG. 4, the light guide connector 8N is plugged into the light source 10, whereupon the light pickup end of the light guide 16N is located in a predetermined position relative to the condenser lens 13. As soon as the source lamp 11 is lit on, illumination light rays are condensed by the reflector mirror 12 and condenser lens 13 to send as much a volume of light to the light guide 16N as possible. The input light rays are picked up by the light guide 16N at angles smaller than its maximum acceptance angle, which is determined by the numerical aperture of the light guide 16N, suppressing light losses during transmission through the light guide 16N to a minimum.

Nextly, in case of the light guide connector 8S with the light guide 16S of a smaller numerical aperture than the light guide 16N, for example, of a numerical aperture of N.A.= 0.55, the adaptor 20S with the concave lens 22S is fitted on the light guide 9S. The socket member 14 is set in position for the light guide rod 9S by anchoring the set screws 34 in the V-groove 33S. In this state, as soon as the light guide rod 9S is connected to the light source 10 as shown in FIG. 3, the input light rays coming in through the condenser lens 13 are not shed directly on the light pickup end face of the light guide 16 but shed thereon indirectly through the corrective lens 22S. Accordingly, by diverging actions of the lens 22S, the input illumination light rays are shed on the light pickup end face of the light guide 16S at a condensing angle which is smaller than the condensing angle θ by the condenser lens 13 and at the same time smaller than the maximum light acceptance angle $θ_s$ of the light guide 16S. Therefore, the light guide 16S is allowed to pick up a maximum volume of the input illumination light to transmit same to the illumination windows efficiently with the least light losses.

On the other hand, in case of the light guide connector 8L with the light guide 16L of a larger numerical aperture than the light guide 16N, for example, of a numerical aperture N.A.=0.87, the adaptor pipe 20L with the corrective lens 22L is threaded on the light guide rod 9L as shown in FIG. 5. On the part of the light source 10, the socked member 14 is fixed in position for the light guide rod 9L by anchoring the set screws 34 in the V-groove 33L. In this state, the light guide connector 8L is plugged into the socket member 14. In this case, by the action of the convex lens 22L, the input light rays incident on the corrective lens 22L at an angle θ are further converged to an angle $θ_L$ which will not exceed the maximum acceptance angle of the light guide 16L. This light supply at a greater angle of incidence makes it possible to widen the angle of illumination light projection from the output end of the light guide 16L for illuminating an intracavitary region uniformly over a broader range, without increasing light losses in transmission through the light guide 16L.

In this way, by the use of the above-described adapters, it becomes possible to supply illumination light at an appropriate light condensing angle from the light source 10 not only to the light guide 16N with a specific numerical aperture suitable for that light source but also to the light guides 16S and 16L which have a smaller or larger numerical aperture, ensuring transmission and projection of illumination light to an intracavitary region under observation in optimum conditions.

As mentioned hereinbefore, the lensless adaptor pipe 20N on the light guide rod 9N is formed in the same size in outer diameter as the adaptor pipes 20S and 20L for the light guide rods 9S and 9L. Therefore, all of these adaptor pipes 20S, 20N and 20L just fit in the aperture 32 in the front plate 31 of the lens housing 30 to hold the optical axis of the light guide in each light guide rod accurately in alignment with that of the condenser lens 13. However, in case the light source 10 employs other positioning mechanism for the light guide rod, of course the light guide rod 9N could be used without fitting the adaptor pipe 20N thereon. Further, when connecting to the light source 10 the light guide 16L of a larger numerical aperture affording a maximum acceptance angle larger than the angles of incident light rays, the adaptor pipe 20L could be dispensed with in a case where there is no need for projecting illumination light over a wider angular range from the output end of the light guide 16L or in a case where illumination light can be diffused to a sufficient degree by the action of an illumination lens which is fitted in each illumination window 5. Moreover, even in case of the light guide with the smallest numerical aperture, it could be connected to a light source without using a corrective lens on the adaptor as long as the light source is adapted to supply illumination light at a condensing angle smaller than the maximum acceptance angle of the light guide. In summary, the adaptor according to the present invention is useful for adjusting the light condensing angle of one light source 10, which is determined by the optical characteristics of the source lamp 11, reflector mirror 12 and condenser lens 13, into agreement with a numerical aperture of a light guide to be connected to the light source 10 for the purpose of creating optimum conditions in transmitting illumination light to and through the light guide and in projecting the illumination light through the illumination windows of the endoscope toward an intracavitary region under observation.

As clear from the foregoing description, the endoscopic light guide connector according to the present invention basically includes an adaptor with a corrective lens to optimize the light condensing angle of a light source in consideration of the numerical aperture of a light guide to be connected to the light source, thereby permitting the light guide to pick up a maximum volume of input light and to create an optimum condition for illumination light projection from its output end toward an intracavitary region under observation, and at the same time permitting to connect various endoscopes with light guides of different numerical apertures to one and same light source in optimum conditions in terms of light transmission and projection.

What is claimed is:

1. A connector device for an endoscopic light guide to be disconnectively connected to a connector socket of an illumination light source having a light condensing lens at a predetermined distance from a source lamp, said connector device comprising:

a light guide rod;

a light guide fitted in said light guide rod and having an input end at a fore end thereof for receiving incident light rays converged to a predetermined light condensing angle through said condensing lens of said light source;

an adaptor pipe fitted on a fore end portion of said light guide rod and connectible to said connector socket of said light source in alignment with optical axis of said light condensing lens;

a light source connector housing;

an adjustor unit movably connected to said light source connector housing and receiving said light guide rod for adjusting a distance between said input end of said light guide and said light condensing lens a corrective lens element arranged in said adaptor pipe for varying angles of converged input light rays coming from said light condensing lens of said light source; and said corrective lens element, in collaboration with said adjustor unit, adjusting an angle of incidence of said input light rays on said input end of said light guide so as to match with a numerical aperture of said light guide.

2. A connector device as defined in claim 1, wherein said corrective lens element is a concave corrective lens when said light guide has a numerical aperture smaller than a predetermined numerical aperture.

3. A connector device as defined in claim 1, wherein said corrective lens element is a convex corrective lens when said light guide has a numerical aperture larger than a predetermined numerical aperture.

4. A connector device as defined in claim 1, wherein said corrective lens element is removable from said adaptor pipe.

5. A connector device as defined in claim 1, wherein said adaptor pipe is detachably threaded on said fore end of said light guide rod.

\* \* \* \* \*